US009085775B2

(12) United States Patent
Marchetti et al.

(10) Patent No.: US 9,085,775 B2
(45) Date of Patent: Jul. 21, 2015

(54) ARTIFICIAL DNA SEQUENCE WITH OPTIMIZED LEADER FUNCTION IN 5' (5'-UTR) FOR THE IMPROVED EXPRESSION OF HETEROLOGOUS PROTEINS IN PLANTS

(75) Inventors: Stefano Marchetti, Pagnacco (IT); Francesca De Amicis, Buttrio (IT); Tamara Patti, Buja (IT)

(73) Assignee: RODINA HOLDINGS S.A., Lugano (CH)

( * ) Notice: Subject to any disclaimer, the term of this patent is extended or adjusted under 35 U.S.C. 154(b) by 594 days.

(21) Appl. No.: 12/521,355

(22) PCT Filed: Dec. 27, 2007

(86) PCT No.: PCT/EP2007/064590
§ 371 (c)(1),
(2), (4) Date: Jun. 26, 2009

(87) PCT Pub. No.: WO2008/080954
PCT Pub. Date: Jul. 10, 2008

(65) Prior Publication Data
US 2011/0041222 A1     Feb. 17, 2011

(30) Foreign Application Priority Data
Dec. 29, 2006  (IT) ............................... UD2006A0280

(51) Int. Cl.
C12N 15/82    (2006.01)
(52) U.S. Cl.
CPC .................................. *C12N 15/8216* (2013.01)
(58) Field of Classification Search
None
See application file for complete search history.

(56) References Cited

U.S. PATENT DOCUMENTS

| | | | |
|---|---|---|---|
| 5,362,865 A | 11/1994 | Austin | |
| 5,659,122 A | 8/1997 | Austin | |
| 5,891,665 A | 4/1999 | Wilson | |
| 6,187,996 B1 | 2/2001 | Ishige et al. | |
| 6,376,747 B1 | 4/2002 | Xing et al. | |
| 6,380,463 B1 | 4/2002 | Jepson | |
| 6,987,179 B1 | 1/2006 | Stuiver et al. | |
| 7,304,209 B2 | 12/2007 | Zink et al. | |
| 2004/0073966 A1 | 4/2004 | Zink et al. | |
| 2006/0008911 A1 | 1/2006 | Beachy | |
| 2006/0074565 A1* | 4/2006 | Miller et al. | 702/20 |
| 2007/0298499 A1 | 12/2007 | Beachy et al. | |
| 2008/0163392 A1 | 7/2008 | Zink et al. | |

FOREIGN PATENT DOCUMENTS

| | | | |
|---|---|---|---|
| EP | 0 566 525 A2 | 10/1993 | |
| EP | 1 078 985 A2 | 2/2001 | |
| KR | 20020092034 A | 12/2002 | |
| WO | 95/06742 A1 | 3/1995 | |
| WO | 97/06268 A2 | 2/1997 | |
| WO | 97/06269 A1 | 2/1997 | |
| WO | 99/31258 A1 | 6/1999 | |
| WO | 02/36787 A2 | 5/2002 | |

OTHER PUBLICATIONS

Gallie et al (PNAS, 86(1), pp. 129-132, 1989; cited in IDS; herein "Gallie1").*
Gallie et al (Nucleic Acids Res., 20(17), pp. 4631-4638, 1992; cited in IDS; herein "Gallie2").*
Bolle et al (The Plant Journal, 6(4), pp. 513-523, 1994).*
Gallie et al (Nucleic Acids Res., 15, pp. 8693-8711, 1987; Gallie3).*
Satoh et al (J. Biosci. and Bioeng., 98, pp. 1-8, 2004).*
"Isolation of Plant DNA from Fresh Tissue", Jeff. Doyle et al., Focus 12, No. 1, pp. 13-15, 1990.
"The GUS reporter gene system", R.A. Jefferson, Nature, vol. 342, Dec. 14, 1989, pp. 837-838.
"Multiple ribosome binding to the 5'-terminal leader sequence of tobacco mosaic virus RNA", Kazimierz Tyc et al., Eur. J. Biochem. 140, pp. 503-511, 1984.
"Non-canonical translation mechanisms in plants: efficient in vitro and in planta initiation at AUU codons of the tobacco mosaic virus enhancer sequence", Jurgen Schmitz et al., Nucleic Acids Research, vol. 24, No. 2, pp. 257-263, 1996.
"Gus fusions: beta-glucuronidase as a sensitive and versatile gene fusion marker in higher plants", Richard A. Jefferson et al., The EMBO Journal, vol. 6, No. 13, pp. 3901-3907, 1987.
"Recursive PCR: a novel technique for total gene synthesis", Chrisostomos Prodromou et al., Protein Engineering, vol. 5, No. 8, pp. 827-829, 1992.
"Synthesis of a modified gene encoding human ornithine transcarbamylase for expression in mammalian mitochondrial and universal translation systems: a novel approach towards correction of a genetic defect", Vanessa C. Wheeler et al., Gene, 169, pp. 251-255, 1996.
"Gene synthesis, high-level expression and assignment of backbone 15N and 13C resonances of soybean leghemoglobin", Stefan Prytulla et al., Federation of European Biochemical Societies (FEBS 17884), letters 399, pp. 283-289, 1996.
"Mutational analysis of the tobacco mosaic virus 5'-leader for altered ability to enhance translation", Daniel R. Gallie et al., Nucleic Acids Research, vol. 16, No. 3, 1988, pp. 883-893.
"Identification of the motifs within the tobacco mosaic virus 5'-leader responsible for enhancing translation", Daniel R. Gallie et al., Nucleic Acids Research, vol. 20, No. 17, pp. 4631-4638, 1992.
"The ribosomal fraction mediates the translational enhancement associated wtih the 5'-leader of tobacco mosaic virus", Daniel R. Gallie et al., Nucleic Acids Research, vol. 16, No. 17, 1988, pp. 8675-8694.
"Efficient Transcription from the Rice Tungro Bacilliform Virus Promoter Requires Elements Downstream of the Transcription Start Site", Gang Chen et al., Journal of Virology, vol. 70, No. 12, pp. 8411-8421, Dec. 1996.

(Continued)

*Primary Examiner* — Elizabeth McElwain
*Assistant Examiner* — Stephen Uyeno
(74) *Attorney, Agent, or Firm* — Novak Druce Connolly Bove + Quigg LLP (57) ABSTRACT

A nucleotide leader sequence 5'-UTR comprises elements favorable to gene expression, such as repeated CAA trinucleotide elements in combination with repeated CT dinucleotide elements.

15 Claims, 2 Drawing Sheets

(56) References Cited

OTHER PUBLICATIONS

"The Scanning Model for Translation: An Update", Marilyn Kozak, The Journal of Cell Biology, vol. 108, pp. 229-241, Feb. 1989.
"Structural Features in Eukaryotic mRNAs That Modulate the Initiation of Translation", Marilyn Kozak, The Journal of Biological Chemistry, vol. 266, No. 30, pp. 19867-19870, Oct. 25, 1991.
"Insertion Mutagenesis to Increase Secondary Structure within the 5'-Noncoding Region of a Eukaryotic mRNA Reduces Translational Efficiency", Jerry Pelletier et al., Cell, vol. 40, pp. 515-526, Mar. 1985.
"Influences of mRNA secondary structure on initiation by eukaryotic ribosomes", Marilyn Kozak, Proc. Natl. Acad. Sci. USA, vol. 83, pp. 2850-2854, May 1986.
Gallie et al., "A Translational enhancer derived from tobacco mosaic virus is functionally equivalent to a Shine-Dalgarno sequence", Proc. Natl. Acad. Sci, USA, vol. 86, pp. 129-132 (1989).
Powell et al., "virG of *Agrobacterium tumefaciens* plasmid pTiC58 encodes a DNA-binding protein", Molecular Microbiology, 3(3), pp. 411-419 (1989).
European Office Action dated May 23, 2011 from European patent application No. 07858186.5 to Universita' Degli Studi di Udine.
XP-002474703-Bolle et al., "Different sequences for 5'-untranslated leaders of nuclear genes for plastid proteins affect the expression of the β-glucuronidase gene" Plant Molecular Biology 32, pp. 861-868, 1996.
De Amicis et al., "Improvement of the PBI121 plant expression vector by leader replacement with a sequence combining a poly (CAA) and a CT motif", Transgenic Res (2007) 16, pp. 731-738, received Jul. 19, 2006, accepted Dec. 4, 2006, published online Jan. 20, 2007.
XP-002474649-Gallie, The 5'-leader of tobacco mosaic virus promotes translation through enhanced recruitment of eIFaF, Nucleic Acids Research, 2002, vol. 30, No. 15, pp. 3401-3411, 2002 Oxford University Press.
XP-002169656-Day et al., "Plant viral leaders influence expression of a reporter gene in tobacco", Plant Molecular Biology 23, pp. 97-109, 1993 Kluwer Academic Publishers.
XP-002474569-Guilley et al., Transcription of Cauliflower Mosaic Virus DNA: Detection of Promoter Sequences, and Characterization of Transcripts, Cell, vol. 30, pp. 763-773, Oct. 1982.
XP-002474570-Yao et al., "Synthetic construct duplicated CaMV 35/TMV omega-prime leader sequence fusion promoter, complete sequence", retrieved from EBI accession No. EMBL:AY183361 Database accession No. AY183361, Feb. 2, 2003.
XP002474571-Yao et al., "An artificial promoter containing many copies of enhancers can increase phytase expression in transgenic rape" computer printout from EBI Dbfetch dated Apr. 1, 2008.
XP002474571—Yao et al., "Synthetic construct multi-copy enhancer promoter element, complete sequence" retrieved from EBI Accession No. EMBL:AY192160; Database accession No. AY192160; Feb. 27, 2003.

\* cited by examiner

SEQUENCE LISTING

<160> NUMBER OF SEQ ID NOS: 7

<210> SEQ ID NO 1
<211> LENGTH: 73
<212> TYPE: DNA
<213> ORGANISM: Artificial
<220> FEATURE:
<221> NAME/KEY: 5' UTR
<222> LOCATION: (1)..(73)
<223> OTHER INFORMATION: synthetic construct

<400> SEQUENCE: 1
acacgtattt ttacaacaat accaacaaca acaacaacaa acaacattac aattacgtat    60
ttctctctct aga    73

```
<210> SEQ ID NO 2
<211> LENGTH: 54
<212> TYPE: DNA
<213> ORGANISM: Artificial
<220> FEATURE:
<223> OTHER INFORMATION: forward primer element for artificial synthesis
      by means of recursive PCR
<220> FEATURE:
<221> NAME/KEY: primer_bind
<222> LOCATION: (1)..(54)
<223> OTHER INFORMATION: forward primer element for artificial synthesis
      by means of recursive PCR

<400> SEQUENCE: 2
gatatctcca ctgacgtaag ggatgacgca caatcccact atccttcgca agac          54

<210> SEQ ID NO 3
<211> LENGTH: 54
<212> TYPE: DNA
<213> ORGANISM: Artificial
<220> FEATURE:
<223> OTHER INFORMATION: reverse primer element for artificial synthesis
      by means of recursive PCR
<220> FEATURE:
<221> NAME/KEY: primer_bind
<222> LOCATION: (1)..(54)
<223> OTHER INFORMATION: reverse primer element for artificial synthesis
      by means of recursive PCR

<400> SEQUENCE: 3
atgaaatgaa cttccttata tagaggaagg gtcttgcgaa ggatagtggg attg          54

<210> SEQ ID NO 4
<211> LENGTH: 53
<212> TYPE: DNA
<213> ORGANISM: Artificial
<220> FEATURE:
<223> OTHER INFORMATION: forward primer element for artificial synthesis
      by means of recursive PCR
<220> FEATURE:
<221> NAME/KEY: primer_bind
<222> LOCATION: (1)..(53)
<223> OTHER INFORMATION: forward primer element for artificial synthesis
      by means of recursive PCR

<400> SEQUENCE: 4
tctatataag gaagttcatt tcatttggag agaacacgta ttttacaac aat           53

<210> SEQ ID NO 5
<211> LENGTH: 52
<212> TYPE: DNA
<213> ORGANISM: Artificial
<220> FEATURE:
<223> OTHER INFORMATION: reverse primer element for artificial synthesis
      by means of recursive PCR
<220> FEATURE:
<221> NAME/KEY: primer_bind
<222> LOCATION: (1)..(52)
<223> OTHER INFORMATION: reverse primer element for artificial synthesis
      by means of recursive PCR

<400> SEQUENCE: 5
taatgttgtt tgttgttgtt gttgttggta ttgttgtaaa aatacgtgtt ct            52

<210> SEQ ID NO 6
<211> LENGTH: 53
<212> TYPE: DNA
<213> ORGANISM: Artificial
<220> FEATURE:
<223> OTHER INFORMATION: forward primer element for artificial synthesis
      by means of recursive PCR
```

```
<220> FEATURE:
<221> NAME/KEY: primer_bind
<222> LOCATION: (1)..(53)
<223> OTHER INFORMATION: forward primer element for artificial synthesis
      by means of recursive PCR

<400> SEQUENCE: 6
aacaacaaca acaaacaaca ttacaattac gtatttctct ctctagagga tcc            53

<210> SEQ ID NO 7
<211> LENGTH: 19
<212> TYPE: DNA
<213> ORGANISM: Artificial
<220> FEATURE:
<223> OTHER INFORMATION: reverse primer element for artificial synthesis
      by means of recursive PCR
<220> FEATURE:
<221> NAME/KEY: primer_bind
<222> LOCATION: (1)..(19)
<223> OTHER INFORMATION: reverse primer element for artificial synthesis
      by means of recursive PCR

<400> SEQUENCE: 7
cacccgggga tcctctaga                                                  19
```

ARTIFICIAL DNA SEQUENCE WITH OPTIMIZED LEADER FUNCTION IN 5' (5'-UTR) FOR THE IMPROVED EXPRESSION OF HETEROLOGOUS PROTEINS IN PLANTS

This application is a §371 National Stage Application of International Application No. PCT/EP2007/064590, filed on 27 Dec. 2007, claiming the priority of Italian Patent Application No. UD2006A000280 filed on 29 Dec. 2006.

FIELD OF THE INVENTION

The present invention concerns an artificial DNA sequence for improving the expression of heterologous proteins in plants.

BACKGROUND OF THE INVENTION

In the field of biotechnology, there is a strongly felt need to enhance the level of expression of genes introduced into the relative organisms. This level is often unsatisfactory, and represents a barrier to the industrial application of innovations in plant and animal biotechnology. There is a quantity of data to support the importance of the leader region in regulating the levels of gene expression, while there are various structural elements that characterize the regulation capacity thereof.

In this case, the untranslated leader sequence in 5' (5'-UTR), as it is proposed in widely diffused vectors (e.g. pBI121 and derivatives, pCAMBIA and derivatives), has numerous defects which make it unsuitable to direct adequate levels of gene expression in genetically modified organisms. In particular, when yields are to be maximized (e.g. the use of plants as cellular factories for compounds useful to man), it is necessary to eliminate the production constraints exerted by the 5'-UTR sequence. To this end, the leader Ω (a sequence that exists naturally in tobacco mosaic virus, TMV) has been proposed in plants. However, this too has imperfections and redundancies that render it open to improvement.

It is known that the region poly(CAA) in the translational enhancer present in the leader Ω of TMV (Gallie and Walbot 1992 Nucleic Acids Res., 20, 4631-4638) significantly enhances the expression levels, that is, it has a positive effect on the translation levels of heterologous proteins in vitro and in vivo (Gallie et al. 1988a Nucleic Acids Res., 16, 883-893, Gallie et al. 1988b Nucleic Acids Res., 16, 8675-8694, Gallie 2002 Nucleic Acids Res., 30, 3401-3411). In the leader Ω, a poly(CAA) sequence is associated with 3 repeats of the sequence ACAATTAC (Gallie et al. 1988a), but detection studies have shown that the regulator element responsible for enhancing the expression levels may consist of a single copy of the sequence ACAATTAC in combination with the motif (CAA)n (Gallie and Walbot 1992).

It is also known that the transcription initiation site (Inr) of the CaMV 35S promoter (Guilley et al. 1982 Cell, 30, 763-773) favours an efficient capping of the mRNA.

Furthermore, it is known that many plant leaders (Bolle et al. 1996 Plant Mol. Biol. 32, 861-868) have a sequence rich in CT elements and that the CT-rich sequences can alter the transcription levels (Chen et al. 1996 J. Virol., 70, 8411-8421).

It is also known that sequences which have a length of more than 40 nucleotides promote the recognition of the first AUG as authentic initial translation codon (Kozak 1989 J. Cell. Biol., 108, 229-241). For example, it has been observed that the extension of the leader from 29 to 74 nt causes an increase in the translation level of mRNA in vitro (Kozak 1991, J. Biol. Chem., 266, 19867-19870) and in vivo (Gallie and Walbot 1992). Leader sequences with a greater content of A/T cause higher expression levels since the formation of segments of double strand mRNA, due to the folding of the molecule over itself, is discouraged. In fact, it is certain that such secondary structures have a depressing effect on the translation efficiency (Pelletier and Sonenberg 1985 Cell, 40, 515-526; Kozak 1986 Proc. Natl. Acad. Sci. USA, 83, 2850-2854). Moreover, it has been noticed that the introduction of portions of 5'-UTRs of viral origin into plant leaders can be reflected in an increase in the level of expression of reporter proteins (Dowson Day et al. 1993 Plant Mol. Biol., 23, 97-109).

Purpose of the present invention is therefore to obviate the shortcomings of the state of the art and to achieve a leader sequence that increases the expression levels of recombinant proteins in plants.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purpose, an artificial DNA sequence having a leader function in 5' (5'-UTR), hereafter indicated by LL-TCK, according to the present invention simultaneously comprises elements favorable to gene expression, such as repeated trinucleotide elements CAA in combination with repeated dinucleotide elements CT.

The LL-TCK sequence according to the present invention was obtained by means of artificial synthesis and is the fruit of the intellect, since it does not exist in nature.

According to an advantageous solution, the LL-TCK sequence according to the present invention provides the combination of trinucleotide elements CAA with dinucleotide elements CT and a modification of the sequences that activate translation present in the leader Ω.

According to a variant, the sequence according to the present invention contains a poly(CAA) region, that is, an oligonucleotide consisting of 2 or more copies of the CAA element, preferably but not necessarily contiguous with each other.

According to another variant, the sequence according to the present invention contains a poly(CT) region, that is, an oligonucleotide consisting of 2 or more copies of the CT element, preferably but not necessarily contiguous with each other.

A variant of the present invention provides that the sequence contains one or more copies of the octamer ACAATTAC.

A sequence obtained from the combination of the sequences with a poly(CAA) region and those with a poly(CT) region also comes within the field of the present invention.

A sequence obtained from the combination of the sequences with a poly(CAA) region and those with one or more copies of the octamer ACAATTACC also comes within the field of the present invention.

Furthermore, a sequence obtained from the combination of the sequences with a poly(CT) region and those with one or more copies of the octamer ACAATTACC also comes within the field of the present invention.

According to the present invention, it is possible to provide a sequence obtained from the combination of the sequences with a poly(CAA) region, those with a poly(CT) region and those with one or more copies of the octamer ACAATTACC.

Furthermore, again according to the present invention, it is possible to provide a sequence obtained from the combination of one or more of the above sequences with the CaMV 35S Inr site, that is, the transcription initiation site of the cauliflower mosaic virus 35S promoter.

The LL-TCK sequence according to the present invention is thus able to increase the expression levels of heterologous proteins in transgenic plants. According to an advantageous solution of the present invention, the new sequence LL-TCK was synthesized so as to create a combination of the following elements according to an original pattern, unique of its kind:
(1) transcription start site (Inr) of the CaMV 35S promoter for an efficient mRNA capping;
(2) poly(CAA) region similar to the translational enhancer present in the TMV leader Ω;
(3) a sequence rich in CT elements, like many plant leaders.

Furthermore, the LL-TCK sequence has a length of more than 40 nucleotides in order to promote the recognition of the first AUG as the authentic translation start codon (Kozak 1989) and an overall content of G+C of less than 40%.

According to a particular solution of the present invention, the LL-TCK sequence is the one shown in SEQ ID NO: 1 (5'-3').

It is possible to foresee that small mutations in the LL-TCK sequence do not alter its effectiveness and for this reason the present invention also refers to leader sequences derived from the present sequence, for example following deletion or duplication of a CAA triplet, substitution or deletion of a single base, etc.

The innovation of LL-TCK consists in the fact that it joins in a single leader a modified poly(CAA) element, an octamer from the TMV leader Ω and a CT-rich sequence of plant origin.

Therefore, the artificial sequence LL-TCK according to an advantageous solution of the present invention provides the presence of a single octamer ACAATTAC associated with 9 CAA repetitions located in position 5' with respect to the octamer.

Since the triplet ATT inside the element ACAATTAC can represent a non-canonical translation start site (Tyc et al. 1984 Eur. J. Biochem., 140, 503-511, Schmitz et al. 1996 Nucleic Acids Res., 24, 257-263), in the LL-TCK leader this triplet has been put in frame with a stop codon.

Furthermore, in the artificial LL-TCK leader an element $(CT)_4$ has been added to the 3' end of the regulator element obtained from the union of the octamer ACAATTAC with the poly(CAA) sequence. The combination of these two elements, for each of which the positive effect on gene expression is known, has never been found in nature or previously made by man.

The LL-TCK leader, combining these two elements, causes an enhancement of both the translation level and the transcription level of the gene concerned.

This effect has been demonstrated by comparing the expression levels of the gene uidA obtained in tobacco plants (Nicotiana tabaccum) transformed with the constructs 35S-LL-TCK::uidA (pSTART) and 35S::uidA (pBI121 with original leader). The vector pSTART was obtained by replacing the leader sequence in pBI121 (Clontech) with LL-TCK. In particular, the object of the replacement and manipulation was the pBI121 sequence comprised between the region Inr (ACACG) and the restriction site Xba I (TCTAGA). The nucleotide sequence flanking the initial translation codon of uidA was kept unvaried in the two constructs so as to prevent variability in the codon AUG recognition.

The choice of using the enzyme beta-glucuronidase (GUS) encoded by the gene uidA as reporter protein was determined by the fact that in tobacco no native GUS-like activity can be observed, and the level of expression of the transgene uidA can be measured by means of a fluorimetric test (Jefferson et al. 1987 EMBO J., 6, 3901-3907) characterized by considerable sensitivity, accuracy, speed and ease of execution.

The fluorimetric readings relating to the enzymatic GUS activity, measured as described by Jefferson (1987) in plants regenerated after transformation (generation $T_1$) have shown how the presence of the LL-TCK leader causes a considerable increase in the expression level of the gene uidA (up to 15 times) compared with the original construct.

The analysis of variance allowed to establish that the differences found between the two populations of tobacco considered (transformed with pSTART and pBI121) are statistically significant, as are the differences between the best expressors of the two groups.

In order to exclude effects deriving from epigenetic variations, the analysis was repeated on the $T_2$ progenies obtained from the self-fertilization of the best primary transformants. In this case too, the plants transformed with pSTART showed expression levels for the gene uidA that were much higher than those obtained with pBI121. In particular, an increase equal to 8.6 times was seen in the activity, considering all the plants in their entirety, and equal to 12.5 times considering only the above-average expressors.

In order to determine the effect of LL-TCK on the transcription of the gene uidA, $T_2$ plants were selected (10 plants for pBI121 and 13 plants for pSTART) characterized by intermediate GUS levels for the analysis of the transcript levels by means of real-time RT-PCR. Starting from the total RNA extracted from each plant, the cDNA used as the template in real-time RT-PCR was synthesized. Two pairs of primers were used (one specific for the gene uidA and one for the endogenous gene of the 18S RNA) and SYBR-Green PCR Master Mix (Applied Biosystems). The correct quantification was made possible by making 2 calibration lines (one for the transgene and one for the endogenous gene) by means of serial dilutions of control plasmids. The transcription level of the gene uidA was then calculated in relative terms for each sample, by means of the percentage ratio between the quantity of mRNA detected for the transgene and the corresponding quantity of ribosomal 18S RNA.

This analysis allowed to verify in the pSTART plants an average transcript level for the gene uidA 1.7 times higher than that found in the pBI121 plants.

For 7 pairs of pSTART and pBI121 plants characterized by similar transcript values, the TEI (translational efficiency index) was calculated. The TEI is equivalent to the ratio between the GUS protein value measured with the fluorimetric assay and the relative standardized mRNA value determined by the real-time RT-PCR. By comparing the TEI, it is clear that the new LL-TCK leader not only has an effect on the mRNA levels, but also causes an increase in the translation efficiency of the mRNA.

The LL-TCK sequence allows to increase the expression level of a heterologous protein by acting both on the level of the mRNA content relating to the gene concerned, and also on the level of the final quantity of protein present.

The LL-TCK effect was studied in tobacco, using the constitutive CaMV 35S promoter and the gene uidA encoding for the enzyme beta-glucuronidase (GUS), but other uses are possible, in combination with other promoters and other genes.

Although in the examples herein reported the LL-TCK leader is used in combination with the CaMV 35S promoter for enhancement of uidA expression in tobacco plants, said leader was successfully used also in tobacco and potato downstream the light-inducible rbcS1 promoter (GenBank Acc. No. AY163904) and in rice downstream the endosperm-specific, phase-dependent glub4 promoter (GenBank Acc. No. AY427571). The genes used in these experiments were those encoding the murine BCL1 antibody, the human beta-glucosidase and a synthetic elastin-like polymer. Since no loss of functionality was recorded in experiments carried out with unrelated genes characterized by a different length, base composition and structure put under the control of promoters with a disparate transcriptional activity and expressed in dicot as well as monocot species, it can be stated that the utility of the LL-TCK leader or similarly composed 5'-UTRs is general, that is, not limited to combinations with certain promoters and/or coding sequences and not limited to certain host species. Therefore, the preferred embodiments of the present invention are comprised in a range of biotechnological applications, including the resistance to biotic/abiotic stresses and herbicides, the production of biofuels, bioplastics, synthetic biopolymers and industrial enzymes, the molecular farming of biopharmaceuticals (e.g. antibodies and their fragments, vaccines, human enzymes, cytokines and growth factors), the improvement of food, feed and fiber quality, the development of reporter and marker gene systems.

Furthermore, it comes within the field of the present invention to construct, inside plant expression vectors, 5'-UTRs in which the following elements are simultaneously present: CaMV 35S Inr site, poly(CAA)n, octamer ACAATTAC, poly(CT)n, where n is any number greater than or equal to 2.

All the possible combinations of the elements that constitute the leader sequence 5'-UTR as expressed above, or in the relative variants, irrespective of their relative positioning 5'-3', come within the field of the present invention Furthermore, the present invention also concerns the sequences complementary to those described above, or the relative variants.

According to a variant, the sequence according to the present invention has a length comprised between 20 and 200 nucleotides, preferably between 40 and 150 nucleotides.

According to a variant, the sequence according to the present invention has a G+C content of less than 60%, preferably less than 50%.

One or more amplification primers also come within the field of the present invention, comprising a nucleotide sequence selected from a group comprising the nucleotide sequences shown in SEQ ID NOS: 2-7 or a complement thereof.

According to another form of execution of the present invention, the sequence according to the present invention can be obtained by:
a) artificial synthesis;
b) natural or induced processes of recombination or mutation inside natural or artificial sequences.

One feature of the present invention also concerns a method for the artificial synthesis of a sequence as described above, using one or more of said amplification primers.

The natural 5'-UTR leader sequences that may be discovered and that appear, to a person skilled in the art, to be non-significant variants, provided they are functionally similar, of the sequence according to the present invention, also come within the field of the present invention.

Sequences deriving from mutation processes of the sequence according to the present invention which appear, to a person of skill, to generate non-significant variants, provided they are functionally similar, of the sequence according to the present invention, are also part of the present invention; the mutations concern irrespectively deletions, insertions, transitions, transversions of one or more nucleotides in the sequence according to the present invention or in the sequence complementary thereto.

The present invention also concerns the bacterial strains carrying plasmids containing the sequence according to the present invention, with particular reference to the species *Escherichia coli, Agrobacterium tumefaciens* and *Agrobacterium rhizogenes*.

The present invention also concerns engineered bacterial strains containing the sequence according to the present invention, irrespective of the type of host organism.

Furthermore, plant cells transformed with expression vectors containing the sequence according to the present invention under the control of a constitutive promoter also come within the field of the present invention.

The following are also covered by the present invention:
  plant cells transformed with expression vectors containing the sequence according to the present invention under the control of a tissue-specific promoter and in particular seed-specific;
  plant cells transformed with expression vectors containing the sequence according to the present invention under the control of an inducible promoter;
  plant cells transformed with expression vectors containing the sequence according to the present invention under the control of a promoter with phase-dependent transcriptional activity;
  plant cells transformed with expression vectors containing the sequence according to the present invention under the control of a promoter active in the chloroplast;
  plant cells transformed with expression vectors containing the sequence according to the present invention under the control of a promoter active in the mitochondrion.

The present invention also comprises plants characterized by the transient expression of any protein whose messenger RNA contains the sequence according to the present invention, transient expression being taken to mean the production of said protein by means of viral vectors, agroinfiltration, electroporation, particle delivery.

The present invention also concerns dicotyledonous plants, with particular reference, but not exclusively, to the species belonging to the families of Solanaceae, Papilonaceae and Cruciferae, stably transformed with expression vectors containing the sequence according to the present invention, and also the progenies of said dicotyledonous plants.

The present invention also concerns monocotyledonous plants, with particular reference, but not exclusively, to the species belonging to the family of Graminaceae (Poaceae), transformed with expression vectors containing the sequence according to the present invention, and also the progenies of said monocotyledonous plants.

The present invention has an advantageous industrial application, since it also concerns the use of the sequence according to the present invention for one or another of the following activities:
  the biotechnological production of molecules;
  the synthesis of recombinant proteins;
  the synthesis of recombinant proteins intended to induce resistance to viral, bacterial or fungal pathogens;
  the synthesis of recombinant proteins intended to induce resistance to herbicides;
  the synthesis of recombinant proteins intended to obtain an altered composition in fatty acids in the raw material and products deriving therefrom;

the synthesis of recombinant proteins intended to obtain an altered nutritional value of the raw material and products deriving therefrom;

the synthesis of recombinant proteins intended for the production of fuels, rubbers and bioplastics;

the synthesis of industrial enzymes and commercial proteins;

the synthesis of pharmaceutical proteins;

the synthesis of orally administered vaccines, intended for men and animals;

the synthesis of injectable vaccines, intended for men or animals;

the synthesis of patient-specific injectable vaccines, preferably idiotype-specific, to be used in treating tumors of the lymphatic system;

the synthesis of proteins involved in the production of secondary metabolites;

the synthesis of proteins used directly or indirectly as factors to identify and/or select transformed cells.

BRIEF DESCRIPTION OF THE DRAWINGS

These and other characteristics of the present invention will become apparent from the following description of some preferential forms of embodiment, given as a non-restrictive example with reference to the attached drawings wherein.

DETAILED DESCRIPTION OF THE PRESENT INVENTION

A) Synthesis of the Artificial Leader Sequence LL-TCK Shown in SEQ ID NO: 1.

A.1) The synthesis of the LL-TCK sequence or similarly composed 5'-UTRs can most conveniently be achieved by artificial synthesis, making use of specialized services available on the market. Due to the limited length of the sequence, it is especially useful to add at each side of the leader a flanking region ending with a restriction site already present within the promoter sequence (5' flanking region) and the coding sequence (3' flanking region). It is obvious to a person skilled in the art that these flanking regions will precisely reproduce the sequence upstream the initiator (Inr) site and the coding sequence, respectively, unless a modification of the promoter and/or the coding sequence is concurrently planned.

A.2) Another procedure to obtain said leader sequence is recursive PCR (Podromou and Pearl 1992 Protein Eng., 5, 827-829, Wheeler et al. 1996 Gene, 169, 251-255, Prytulla et al. 1996 FEBS Letters, 399, 283-289).

Once the LL-TCK sequence or a similarly composed 5'-UTR is obtained by either method, leader variants can easily be produced by PCR or any other procedure developed for random or in situ mutagenesis.

In this example, the description of the LL-TCK synthesis by recursive PCR for its insertion into pBI121 (GenBank accession no. AF485783), in particular between the CaMV 35S promoter and the uidA coding sequence, is reported.

Five synthetic oligonucleotides were used as primers, having a length comprised between 42 and 54 nt and a partial overlapping degree equal to 24 nt, and a terminal reverse primer of 19 nt, shown respectively in the sequences SEQ ID NOS: 2, 3, 4, 5, 6 and 7.

Figure 5:
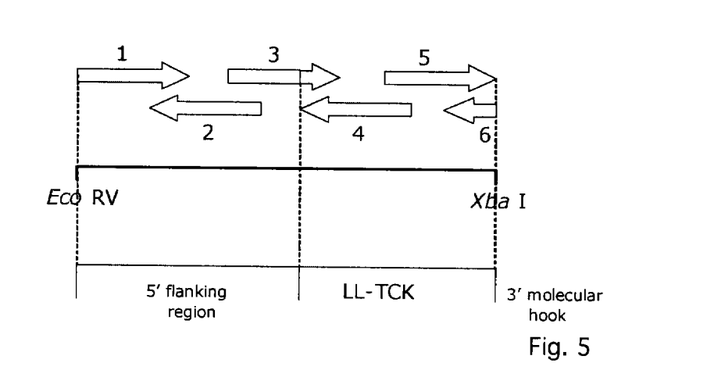
FIG. 5 is a diagram of the overlapping of reverse and forward primers for the synthesis of LL-TCK by means of recursive PCR.

All primers are written in the 5'-3' direction. The sequences SEQ ID NOS: 2, 4, 6 are forward primers, while the sequences SEQ ID NOS: 3, 5 and 7 are reverse primers. Forward and reverse primers overlap each other according to the diagram in FIG. 5.

To facilitate the handling and the insertion of LL-TCK into the vector sequence concerned, a terminal portion starting with an Eco RV site was added in 5', while a single Xba I site was added to the 3' edge.

Therefore, the primers were designed so as to provide the reconstruction of the portion 3'-terminal of the promoter 35S (from the Eco RV site to the Inr region) in order to facilitate the subsequent insertion into the vector pBI121 (Clontech).

The external reverse primer introduces the Xba I site to the terminal 3', whereas in 5' the Eco RV site is used.

In pBI121, these sites fall inside the CaMV 35S promoter and in proximity with the translation start signal of uidA, respectively. Therefore, the synthesis was provided of the desired sequence and the cloning to replace the fragment [Eco RV-Xba I].

The primers comprising the nucleotide sequences shown in SEQ ID NOS: 2-7 were designed and created to confirm the promoter sequence in the region between the Eco RV site and the initiator site of CaMV 35S, to synthesize the LL-TCK leader and provide a molecular hook to the terminal 3' for cloning.

The synthesis of LL-TCK was performed by a single PCR, using a PCR reaction mixture in which the concentration of the external primers, SEQ ID NOS: 2 and 7 (corresponding to the two ends of the synthesized segment) was 100 times greater than that of the internal primers SEQ ID NOS: 3, 4, 5 and 6.

In order to achieve a higher fidelity in DNA synthesis, a proof-reading DNA polymerase was used in combination with a 50% reduction of dNTPs concentration.

The PCR reaction mixture is as follows:
10×Pfu Buffer containing 15 mM $Mg^{2+}$: 10 microL
Primer SEQ ID NO: 2 [10 microM]: 2 microL
Primer SEQ ID NO: 3 [0.1 microM]: 2 microL
Primer SEQ ID NO: 4 [0.1 microM]: 2 microL
Primer SEQ ID NO: 5 [0.1 microM]: 2 microL
Primer SEQ ID NO: 6 [0.1 microM]: 2 microL
Primer SEQ ID NO: 7 [10 microM]: 2 microL
Pfu DNA polymerase [3 U/microL]: 0.8 microL
dNTPs [2.5 milliM each]: 4 microL
Water to a final volume of 100 microL.

In particular, for DNA synthesis and amplification, the Taq polymerase Pfu (Promega) was used, and the following cycle: 1×(95° C. for 5 min); 40×(95° C. for 15 sec; 48° C. for 30 sec; 72° C. for 20 sec); 1×(72° C. for 7 min).

The PCR product was purified by ethanol precipitation, electrophoresed in a 1% agarose gel in TAE buffer, recovered from gel with the aid of a commercial kit, A-tailed with AmpliTaq Gold™, and ligated into pGEM®-T (Promega) for sequencing on both strands.

The ligation mixture was used to transform competent cells of *Escherichia coli*, strain JM101. The absence of any mismatch between the cloned and the designed sequence was verified by sequencing on double strand.

B) Construction of a Plant Expression Vector Harbouring the LL-TCK Sequence

Figure 1:
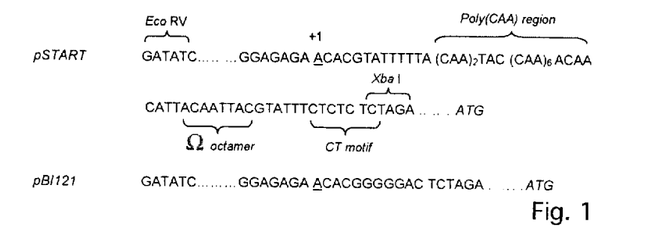
FIG. 1 is a comparison between the leader sequences in pBI121 and in pSTART, wherein the transcription start site is underlined. Since the sequences between the Eco RV site and the transcription start site and between the Xba I site and the uidA ATG triplet are identical in pSTART and in pBI121, they have been partly omitted (dots)
Figure 2:
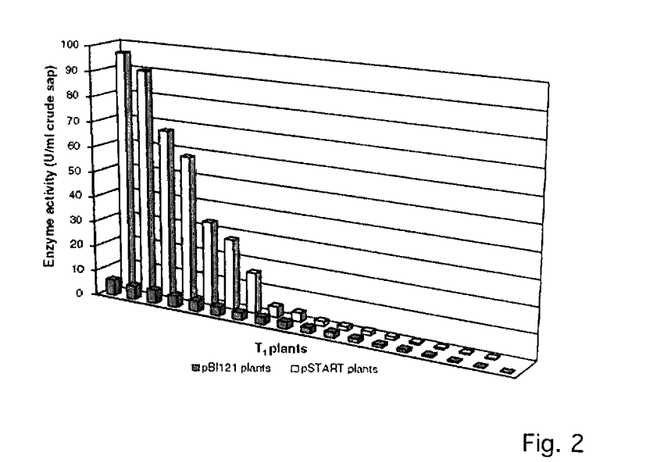
FIG. 2 shows the expression levels of beta-glucuronidase (GUS) in the transgenic $T_1$ plants.

The possible addition of flanking regions or molecular hooks to the LL-TCK sequence or similarly composed 5'-UTRs offers a broad range of cloning solutions in expression vectors of different kind. In this example, the method used to clone the [Eco RV-Xba I] fragment of Example 1 in substitution of the [Eco RV-Xba I] fragment of pBI121 (GenBank accession no. AF485783) is described. Since pBI121 has multiple Eco RV sites beyond that inside the CaMV 35S promoter, the latter promoter was excised from pBI121 (Clontech) (Jefferson et al. 1987) making use of the Hind III and Xba I restriction enzymes.

The fragment was recovered from 1% agarose gel in TAE buffer and subcloned in pUC18 (Pharmacia, GenBank accession no. L08752), previously digested with the same enzymes.

As we said, this passage was necessary because pBI121 has multiple Eco RV sites. The pUC18/35S vector obtained was used to make the new combination of 35S promoter—LL-TCK leader.

The LL-TCK sequence was excised from the pGEM-T vector by means of digestion with Eco RV and Xba I (NEB), separated from the vector sequence by agarose gel electrophoresis and subsequently recovered from gel with the aid of a commercial kit. The pUC18/35S vector was in turn digested with the same enzymes, treated with alkaline phosphatase (Pharmacia), electrophoresed and recovered from gel as above. Then a ligation reaction was carried out at 4° C. for 16 hours in the presence of T4 DNA ligase (Promega). In particular, 3.5 ng of the [Eco RV-Xba I] fragment were combined with 25 ng of the vector in the presence of 1 U T4 DNA ligase in a volume of 10 microL containing a suitable reaction buffer.

The pBI121 vector (Clontech) was subjected to digestion with Xba I and Hind III (NEB) to remove the CaMV 35S promoter. The complex 35S-LL-TCK was in turn excised from the cloning vector pUC18 by means of digestion with the same enzymes; the pBI121 vector frame and the 35S-LL-TCK insert were electrophoresed and recovered from gel as above. Finally, a ligation of 35S-LL-TCK in the pBI121 framework was performed, obtaining the vector pBI121/35S-LL-TCK::uidA::NOS to which the name pSTART (FIG. 1) was assigned.

C) Transformation of Plants with an Expression Vector Containing the LL-TCK Sequence Transgenic plants harbouring the LL-TCK sequence or similarly composed 5'-UTRs can be produced through a range of methods, including coinfection with engineered strains of *Agrobacterium* spp., infection or trasfection with engineered strains of phytoviruses, electroporation, particle delivery, DNA microinjection.

The pSTART expression vector was electroporated into *Agrobacterium tumefaciens* strain EHA 105 and the transformed *Agrobacterium* cells used for tobacco (*Nicotiana tabacum* L., cv. Xanthi) transformation. Briefly, 2 ml LB medium supplemented with kanamycin (50 mg/L) were inoculated with transformed *Agrobacterium* cells. Bacterial cultures were incubated at 29° C. for 16 hours. Leaf discs (7 mm in diameter) were obtained with a cork borer from axenically grown, 30-d old seedlings or from mature leaves collected from plants at the late-rosette stage. In the latter case, tobacco leaves were rinsed with distilled water, surface-sterilized in 1% sodium hypochlorite for 5 min and in 95% ethanol for 30 sec and blotted to sterile filter paper under a laminar flow hood.

Leaf discs were placed in a Petri dish containing 15 mL of Murashige and Skoog medium supplemented with 0.1 mg/L naphthalene acetic acid (NAA), 1 mg/L 6-benzyladenine (BA), 30 g/L sucrose and solidified with 8 g/L agar. Immediately after this transfer, 2 ml of the above-mentioned *Agrobacterium* culture were poured in the Petri dish and the leaf discs were uniformly wetted. After removal of the LB medium in excess, the dish was sealed and incubated for 24 hours at 25° C. in the light (30.5 microE/square meter/sec).

Leaf discs were then transferred to a new Petri dish containing 15 mL of Murashige and Skoog medium supplemented with 0.1 mg/L naphthalene acetic acid (NAA), 1 mg/L 6-benzyladenine (BA), 500 mg/L cefotaxime, 30 g/L sucrose and solidified with 8 g/L agar. They were incubated for a week at 28° C. and illuminated for 16 hours/day; they were eventually transferred to a substrate identical to the former except for the presence of 200 mg/L kanamycin. Explants were subcultured every 3 weeks; regenerated shoots were isolated from callus tissue and rooted on semisolid Murashige and Skoog medium supplemented with 2 mg/L indole-3-butyric acid, 500 mg/L cefotaxime, 200 mg/L kanamycin, 30 g/L sucrose.

Putative transgenic plants were potted in peat and grown in a greenhouse under Powerstar HQI-T lamps (Osram) (200 mM photons/square meter/sec at canopy level) for 16 hours/day at 25° C./19° C. light/dark.

In this example, transformation was confirmed by PCR and beta-glucuronidase assays. For PCR assay, total DNA was extracted according to Doyle and Doyle (1990) and the following primers were used:

```
Forward     5'- ACAATTACGTATTTCTCTCTCTAGA -3'
Reverse     5'- CGATCGGGGAAATTCGAGCTC -3'
```

The forward and reverse primers anneal to the end of the LL-TCK sequence and to part of the NOS terminator, respectively and do not give rise to any amplification product in untransformed Xanthi plants (in transgenic plants the amplicon length is 1936 bp, as expected).

About 93% of the regenerated plants were found transgenic when a standard reaction mix was formed and the following temperature cycling was used: 1×(94° C. for 5 min); 40×(94° C. for 1 min 15 sec; 60° C. for 45 sec; 72° C. for 2 min); 1×(72° C. for 5 min).

Plant transformation was further demonstrated by GUS histochemical assays (Jefferson et al. 1987) and fluorimetric determination of GUS activity. Controls consisted of Xanthi plants raised in vitro from uninfected discs. The methods used for the fluorimetric assay and the results obtained are reported in detail in point D.

The same procedure was followed to produce and characterize transgenic plants harbouring the original leader sequence. Ceteris paribus, no effect of the LL-TCK sequence was noted upon regeneration and transformation rates.

D) Effect of the LL-TCK Sequence on Transgene Expression Levels As previously indicated, the plasmids pBI121 and pSTART were individually used for *Agrobacterium*-mediated transformation of tobacco leaf discs. Since in both cases the gene under control is uidA (also known as gusA), transgene expression levels achievable with LL-TCK and the widely-distributed pBI121 leader can be compared directly by determining the activity of the uidA encoded enzyme, beta-glucuronidase (EC 3.2.1.31). About twenty primary transformants (that is transgenic plants belonging to the first generation, $T_1$) of each population were assayed for transgene presence by PCR and subsequently analysed for beta-glucuronidase activity (FIG. 2). When the late rosette stage was reached (30 days upon hardening), the 3 youngest leaves were collected from each plant to obtain crude sap by pressing (Erich Pollähne); 100 microL of crude sap were mixed with 2 volumes of extraction buffer (Jefferson 1989) containing 12 mg of high molecular weight polyvinyl pyrrolidone (PVP). After centrifugation for 15 min at 11,500×g, the supernatant was collected and analysed fluorimetrically (Dyna Quant 200 Fluorometer; GE Healthcare) in duplicate using 4-methylumbelliferyl-beta-D-glucuronide (MUG; Sigma-Aldrich) as substrate. Trials were made to determine the background noise due to intrinsic fluorescence of the samples, quenching, as well as substrate degradation by factors other than the recombinant enzyme. The level of transgene expression was measured in terms of beta-glucuronidase units per mL of crude sap, one unit being defined as the amount of enzyme releasing 1 nM 4-methylumbelliferone (4-MU) $\min^{-1}$ using the same assay conditions as previously described (Jefferson 1989). Data were submitted to a log transformation to avoid any correlation between variance and mean; the analysis of variance was carried out after checking the normality of the distribution of log data by means of the Kolmogorov-Smirnov test and the homogeneity of variances with Bartlett's formula. Averages were compared with Duncan's multiple range test at the probability level, P=0.05.

The analysis of variance carried out on fluorescence data showed the absence of any significant variation among young leaves of the same plant, whereas remarkable differences existed among plants. Specifically, the synthetic leader determined a highly significant increase (up to 15-fold) in uidA expression (Table 1).

TABLE 1

Beta-glucuronidase activity (U/mL of crude sap) in randomly-chosen $T_1$ plants

| pSTART | pBI121 |
|---|---|
| 96.10 | 6.24 |
| 89.81 | 5.37 |
| 67.06 | 5.34 |
| 57.89 | 4.52 |
| 33.16 | 4.20 |
| 27.62 | 3.55 |
| 15.97 | 2.95 |
| 4.24 | 2.89 |
| 3.51 | 2.79 |
| 1.85 | 2.34 |
| 1.64 | 2.30 |
| 1.46 | 1.62 |
| 1.21 | 1.17 |
| 0.77 | 1.12 |
| 0.64 | 0.75 |
| 0.46 | 0.47 |
| 0.38 | 0.23 |
|  | 0.15 |

To demonstrate that these outcomes were not biased by epigenetic variation, analyses were repeated on $T_2$ progenies. In particular, the best 4 $T_1$s in each population were selfed and the resulting seed plated on a kanamycin-enriched medium for selection; 5-7 resistant $T_2$ plants were randomly chosen within each progeny and raised to the late rosette stage for verification of the transgene presence by PCR and measurement of beta-glucuronidase activity by fluorimetric assays; enzyme levels were again expressed as units per mL of crude sap but also as units per mg total protein (as determined by Bradford assay) to account for plant-to-plant variation in metabolism.

Figure 3:
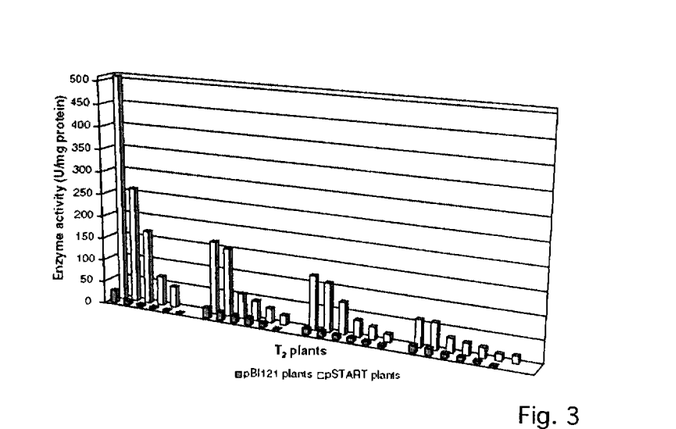
FIG. 3 shows the expression levels of beta-glucuronidase (GUS) in the transgenic $T_2$ plants; the plants are grouped into four groups, each representing sister plants which descend from the best $T_1$ transformants. Least Significant Difference (P=0.01)=4.7 U/mg of total protein.

Similarly to what observed in the $T_1$ generation, transgenic $T_2$ plants harbouring the new leader showed significantly higher levels of uidA expression (FIG. 3); as compared to the pBI121 leader, a 8.6-fold and a 12.5-fold increase of activity were estimated taking into account the whole plant population or the above-average expressors, respectively (Table 2).

TABLE 2

Beta-glucuronidase activity (U/mg protein) in $T_2$ plants obtained from the best 4 $T_1$s

| pSTART | pBI121 |
|---|---|
| 139.07 | 789 |
| 71.27 | 5.17 |
| 45.43 | 4.44 |
| 44.81 | 3.96 |
| 41.67 | 3.94 |
| 32.92 | 3.78 |
| 29.81 | 3.77 |
| 19.79 | 3.58 |
| 18.04 | 3.55 |
| 16.40 | 3.23 |
| 15.10 | 3.15 |
| 13.55 | 3.09 |
| 12.84 | 2.94 |
| 12.32 | 2.62 |
| 10.78 | 2.45 |
| 10.02 | 1.71 |
| 9.00 | 1.28 |
| 8.50 | 1.22 |
| 6.98 | 1.14 |
| 6.57 | 0.64 |
| 5.39 | 0.52 |
| 5.16 | 0.46 |
| 5.01 | 0.44 |
| 3.17 | 0.31 |

E) Effect of the LL-TCK Sequence on Gene Transcription and Translation

The combination of different elements in LL-TCK or similarly composed 5'-UTRs reflects in measurable improvements of transcriptional as well as translational efficiency of a given transgene. In this example, such improvements are shown in transgenic $T_2$ tobacco plants obtained with pBI121 and pSTART, as described before. In order to collect such evidence, plants belonging to the pBI121 or the pSTART group (10 and 13 $T_2$s, respectively) and characterized by intermediate uidA expression levels were analysed to determine:

i. the mean transcript levels of uidA;
ii. the mean transcript levels of 18S RNA;
iii. the amount of beta-glucuronidase actually produced.

To minimize experimental error, one young leaf was collected from each plant and cut in two, one half being used for RNA isolation, the other for beta-glucuronidase assay.

Total RNA was extracted with RNAgents Total RNA Isolation System (Promega). First-strand cDNA was synthesized from 1 microg RNA by AMV Reverse Transcriptase (Promega) in the presence of random primers. The cDNA synthesis reaction was diluted 1:5 and 1 microL was used for real-time PCR (qRT-PCR).

qRT-PCRs were performed making use of SYBR-Green PCR Master Mix (Applied Biosystems) and specific primers each at a 0.3 microM final concentration. All reactions were carried out with the iCycler iQ multicolor real-time PCR detection system (Bio-Rad) and run with the following program: 1×(95° C. for 10 min); 50×(95° C. for 15 sec; 62° C. for 30 sec; 72° C. for 30 sec). To amplify the uidA transcript, the following primers were used:

```
Forward    5'-TTACGCTGAAGAGATGCTCGAC-3'
Reverse    5'-CCTAAAGAGAGGTTAAAGCCGACAG-3'
```

For the 18S RNA target sequence, the primers were designed on the basis of GenBank accession n. AJ236016:

```
Forward    5'-ACATCCAAGGAAGGCAGCAG-3'
Reverse    5'-GACTCATAGAGCCCGGTATTGTTATT-3'
```

In both cases, the amplicon length was 90 bp. In each PCR run, serial dilutions of control plasmids were included in parallel with known amounts of input copy number in order to draw standard calibration curves. Specifically, 10-fold serial dilutions (from $10^5$ to $10^2$ copies) of the uidA-harbouring plasmid pBI221, were used as templates. For the same purpose, a 550 bp fragment of the 18S RNA gene (AJ236016) was cloned in pGEM-T Easy (Promega) and used in the range of $10^8$-$10^5$ copies.

The starting quantities of uidA transcript and control RNA were determined with ICycler IQ real-time detection system software ver. 3.0. For each sample, at least 3 independent estimates were performed; in all cases, the maximum value for the variation coefficient (VC=SD/mean) was fixed at 20%. The % ratio between the mean transcript levels of uidA and 18S RNA was calculated for each sample. To standardize data, the highest uidA transcript level was considered equal to 1.00 and values recorded for each transgenic plant were expressed accordingly.

Results obtained in qRT-PCR indicated that the substitution of the pBI121 leader with LL-TCK determines a clear increase of average uidA transcript levels. Specifically, the transcriptional efficiency was found 1.7-fold higher in plants harbouring the LL-TCK leader (Table 3).

TABLE 3

% ratio between uidA and 18S transcripts in several $T_2$ plants

| pSTART | pBI121 |
|---|---|
| 0.01371% | 0.00881% |
| 0.01189% | 0.00832% |
| 0.01132% | 0.00761% |
| 0.00968% | 0.00437% |
| 0.00960% | 0.00315% |
| 0.00896% | 0.00308% |
| 0.00578% | 0.00282% |
| 0.00556% | 0.00234% |
| 0.00425% | 0.00225% |
| 0.00315% | 0.00158% |
| 0.00272% | 0.00072% |
| 0.00201% | |
| 0.00189% | |

Figure 4A:
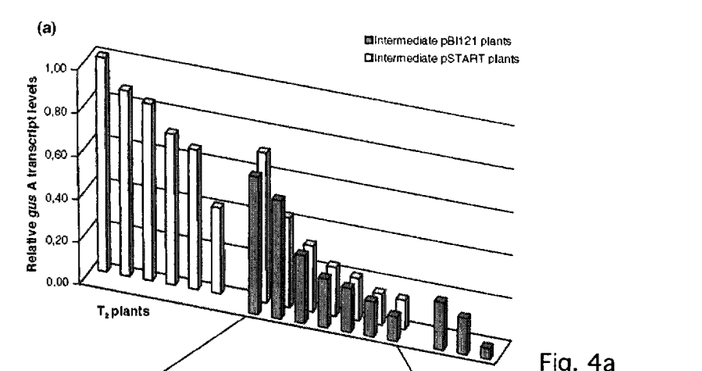
FIG. 4a shows the relative transcript levels of uidA (gusA) as determined by real-time RT-PCR in $T_2$ plants obtained with pSTART and pBI121 characterized by intermediate beta-glucuronidase expression levels. The seven pairs of plants with similar transcript levels are identified.
Figure 4B:
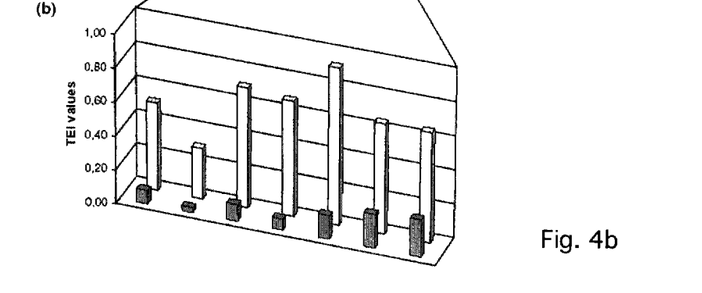
FIG. 4b shows the values of the translation efficiency index (TEI) for the $T_2$ plants with similar transcript levels. TEI was calculated as follows: for each transformant, the concentration of beta-glucuronidase (GUS) [U/mg of total protein] was divided by the relative standardized level of mRNA; the highest TEI was considered equal to 1.00 and the values recorded for each transgenic plant were expressed accordingly.

In addition, after having identified 7 plant couples with nearly overlapping uidA transcript levels (FIG. 4a), a translational efficiency index (TEI) was attributed to each plant (FIG. 4b), making the ratio between beta-glucuronidase concentration and the relative standardized level of uidA transcript. By comparison of TEI values, the two leaders were found to determine a clearly different translational efficiency of uidA transcripts, which was greater using the leader according to the present invention (Table 4).

TABLE 4 ratio between GUS enzymatic activity and relative transcription level of uidA gene measured in some $T_2$ plants

| TEI | pSTART | pBI121 | TEI |
|---|---|---|---|
| 1.00 | 299.07 | 103.06 | 0.34 |
| 0.93 | 277.07 | 66.58 | 0.22 |
| 0.71 | 211.87 | 58.52 | 0.20 |
| 0.68 | 203.76 | 19.82 | 0.07 |
| 0.65 | 195.24 | 42.97 | 0.14 |
| 0.65 | 194.12 | 47.18 | 0.16 |
| 0.52 | 154.91 | 20.86 | 0.07 |
| 0.34 | 102.01 | 29.52 | 0.10 |
| 0.30 | 89.48 | 8.94 | 0.03 |
| 0.27 | 80.26 | 12.34 | 0.04 |
| 0.25 | 73.69 | 22.81 | 0.08 |
| 0.20 | 59.70 | | |
| 0.17 | 49.40 | | |

The invention claimed is:

1. A 5'-UTR leader sequence comprising SEQ ID NO: 1.

2. A DNA construct comprising the 5'-UTR leader sequence of claim 1 operably linked upstream to a nucleic sequence coding for a heterologous protein, wherein said 5'-UTR Leader sequence is effective for enhancing expression of said heterologous protein in plants.

3. A plant expression vector comprising a 5'-UTR leader region, wherein said 5'-UTR leader region comprises the sequence shown in SEQ ID NO: 1.

4. The sequence of claim 1, obtained from artificial synthesis.

5. A bacterial strain carrying plasmids containing the sequence as in claim 1.

6. An engineered virus strain containing the sequence as in claim 1, irrespective of the host organism.

7. A plant cell transformed with expression vectors containing the sequence as in claim 1, under the control of a promoter selected from a group consisting of: a constitutive promoter, a tissue-specific promoter, an inducible promoter, a promoter with phase-dependent transcriptional activity, a promoter active in the chloroplast, and a promoter active in the mitochondrion.

8. A plant characterized by the transient expression of any protein in which the RNA messenger contains the sequence as in claim 1, transient expression being taken to mean the production of said protein by means of viral vectors, agroinfiltration, particle delivery, or electroporation.

9. A plant, or progeny thereof, stably transformed with expression vectors containing the sequence as in claim 1.

10. A method comprising expressing the DNA construct of claim 2 to synthesize said heterologous protein.

11. The method of claim 10, wherein the heterologous protein
    induces resistance to viral pathogens, bacterial pathogens, fungal pathogens, or herbicides.

12. The method of claim 10, wherein the heterologous protein is selected from the group consisting of proteins involved in the production of secondary metabolites, proteins usable directly or indirectly as factors to identify and/or select transformed cells, and pharmaceutical proteins.

13. A method comprising expressing the DNA construct of claim 2 to synthesize at least one member selected from the group consisting of industrial enzymes, commercial proteins, orally administered vaccines, or injectable vaccines.

14. A method comprising expressing the DNA construct of claim 2 to synthesize patient-specific injectable vaccines to treat tumors of the lymphatic system.

15. The bacterial strain of claim 5, wherein said bacterial strain is a strain of the species *Escherichia coli*, *Agrobacterium tumefaciens* or *Agrobacterium rhizogenes*.

* * * * *